United States Patent [19]

Tesmann et al.

[11] Patent Number: 5,034,159

[45] Date of Patent: Jul. 23, 1991

[54] AQUEOUS SURFACTANT SOLUTIONS THICKENED WITH AN ADDUCT OF ETHYLENE OXIDE OR PROPYLENE OXIDE AND A $C_8$-$C_{22}$ FATTY ALCOHOL

[75] Inventors: Holger Tesmann, Duesseldorf; Hermann Hensen, Haan; Wolfgang Hochschon, Hilden; Uwe Ploog, Haan; Ansgar Behler, Bottrop, all of Fed. Rep. of Germany

[73] Assignee: Henkel Kommanditgesellschaft auf Aktien, Duesseldorf, Fed. Rep. of Germany

[21] Appl. No.: 355,214

[22] Filed: May 22, 1989

[30] Foreign Application Priority Data

May 21, 1988 [DE] Fed. Rep. of Germany ....... 3817415

[51] Int. Cl.$^5$ .......................... C11D 1/66; C11D 1/00
[52] U.S. Cl. ............... 252/551; 252/174.21; 252/174.23; 252/174.25; 252/DIG. 5; 252/DIG. 14
[58] Field of Search ............... 252/DIG. 14, DIG. 5, 252/174.21, 174.25, 551, 174.23, DIG. 15

[56] References Cited

U.S. PATENT DOCUMENTS

| | | | |
|---|---|---|---|
| 4,071,475 | 1/1978 | Iijima et al. | 252/545 |
| 4,226,736 | 10/1980 | Bush et al. | 252/135 |
| 4,564,463 | 1/1986 | Secemski et al. | 252/174.17 |
| 4,592,875 | 6/1986 | Kesling, Jr. et al. | 252/551 |
| 4,772,427 | 9/1988 | Danson et al. | 252/559 |
| 4,883,610 | 11/1989 | Ciallella | 252/559 |

FOREIGN PATENT DOCUMENTS

| | | |
|---|---|---|
| 0006105 | 1/1980 | European Pat. Off. . |
| 0026544 | 4/1981 | European Pat. Off. . |
| 0026546 | 4/1981 | European Pat. Off. . |
| 0082569 | 6/1983 | European Pat. Off. . |
| 0092256 | 10/1983 | European Pat. Off. . |
| 0115083 | 8/1984 | European Pat. Off. . |
| 3706047 | 9/1988 | Fed. Rep. of Germany . |
| 3719968 | 12/1988 | Fed. Rep. of Germany . |

OTHER PUBLICATIONS

Soap/Cosmetics/Chemical Specialties, Jan. 1988, p. 34.

*Primary Examiner*—Prince E. Willis
*Assistant Examiner*—J. Silbermann
*Attorney, Agent, or Firm*—Ernest G. Szoke; Wayne C. Jaeschke; Real J. Grandmaison

[57] ABSTRACT

Adducts of ethylene oxide and/or propylene oxide with saturated and/or unsaturated $C_{8-22}$ fatty alcohols having an average degree of alkoxylation n of 1 to 10, and more especially 1 to 6, are particularly suitable as thickeners for aqueous surfactant solutions when the adducts have a narrow homolog distribution compared with the products obtained by standard methods.

13 Claims, No Drawings

AQUEOUS SURFACTANT SOLUTIONS THICKENED WITH AN ADDUCT OF ETHYLENE OXIDE OR PROPYLENE OXIDE AND A $C_8$-$C_{22}$ FATTY ALCOHOL

BACKGROUND OF THE INVENTION

1. Field of The Invention

This invention relates to aqueous surfactant solutions containing special thickeners.

Aqueous surfactant solutions, particularly those used in the field of body care as shampoos, bubble baths, shower baths, hand washing pastes and the like, generally contain anionic surfactants such as alkyl ether sulfates, for example, as surfactant components. To stabilize these clear or disperse surfactant solutions and to improve their handling properties, thickeners are normally added.

Several inorganic and organic compounds which are used to increase the viscosity of aqueous solutions containing anionic surfactants are already known to the expert.

A number of water-soluble salts, such as sodium chloride for example, may be used as inorganic thickeners. Organic thickeners include, inter alia, fatty acid alkanolamides such as coconut oil fatty acid monoethanolamide, lauric acid monoethanolamide, oleic acid diethanolamide and coconut oil fatty acid diethanolamide, polyethylene glycol difatty acid esters and a number of water-soluble polymers.

Where inorganic salts alone are used, the desired viscosity in the surfactant solution can in general only be built up, if at all, by using high concentrations. Accordingly, it is normally necessary to use the inorganic salts in conjunction with organic thickeners which are attended by a number of disadvantages. For example, the solutions thickened with polyethylene glycol fatty acid diesters often show inadequate viscosity stability in storage while water-soluble polymers are often poorly soluble and produce unwanted, slimy flow behavior with a tendency towards "stringing". Fatty acid alkanolamides are becoming increasingly undesirable in cosmetic preparations because a small production-induced content of free alkanolamines can give rise to nitrosamine formation.

2. Discussion of Related Art

Accordingly, it has been proposed in German patent application P 37 30 179.9 to use adducts of ethylene oxide and/or propylene oxide with unsaturated fatty alcohols to thicken surfactant solutions. These products are not attended by the disadvantages mentioned above. However, there is a need for thickeners which have an increased thickening effect for comparable properties. For a given thickener content, this would facilitate the production of systems having relatively high viscosity and reduction of the thickener content for a given viscosity.

DESCRIPTION OF THE INVENTION

Other than in the operating examples, or where otherwise indicated, all numbers expressing quantities of ingredients or reaction conditions used herein are to be understood as modified in all instances by the term "about".

It has now surprisingly been found that the problem as stated above can be solved by using as thickeners adducts of ethylene oxide and/or propylene oxide with saturated and/or unsaturated $C_{8-22}$ fatty alcohols having average degrees of alkoxylation n of 1 to 10 and more especially 1 to 6, which have a particular homolog distribution (oligomer distribution).

It is known to the expert that alkoxylation reactions such as, for example, the addition of n mol of ethylene oxide onto 1 mol of fatty alcohol by known ethoxylation processes do not give a single adduct, but rather a mixture of residual quantities of free fatty alcohol and a number of homologous (oligomeric) adducts of 1,2,3, .. . n, n+1, n+2 ... etc. molecules of ethylene oxide per molecule of fatty alcohol. The average degree of ethoxylation (n) is defined by the starting quantities of fatty alcohol and ethylene oxide. The distribution curve of the homolog mixture generally shows a maximum between n−3 and n+3. Further information on these points can be found, for example, in the journal Soap/Cosmetics/Chemical Specialties, January, 1988, page 34.

Accordingly, the present invention relates to thickened aqueous surfactant solutions containing water-soluble ionic surfactants and nonionic surfactants as thickeners, characterized in that the nonionic surfactants used are adducts of ethylene oxide and/or propylene oxide with saturated and/or unsaturated $C_{8-22}$ fatty alcohols having average degrees of ethoxylation n of 1 to 10 and more especially 1 to 6, the adducts possessing a narrow-range homolog distribution in the sense that they contain significantly fewer homologs containing more than n+3 mol of ethylene oxide and/or propylene oxide than the adducts obtained in the reaction of fatty alcohols with ethylene oxide and/or propylene oxide using approximately 0.1 to 1% by weight alkali metal alcoholate, alkali metal hydroxide or alkali metal as catalyst at temperatures of 120° to 220° C. and under pressures of up to 5 bar. In the present context, the expression "significantly fewer" is to be understood to mean that the content of the homologs mentioned is reduced by an amount which is clearly outside the accuracy of measurement of the analytical method used, i.e. is generally greater than 5% of the content of these homologs.

According to the invention, preferred thickeners are adducts of which the homolog content, at more than n+3 mol of ethylene oxide and/or propylene oxide, is reduced by more than 10% and, in particular, by more than 30% compared with the products produced by the process mentioned above. Adducts in which the content of the homologs mentioned is reduced by more than 50% show particularly good thickening effects. Although it is possible in principle to prepare and use in accordance with the invention adducts which are almost completely free from homologs containing more than n+3 mol ethylene oxide and/or propylene oxide, products in which the content of the homologs mentioned is preferably reduced by at most 90% and more especially by at most 75% are used in practice. Accordingly, in the thickeners according to the invention, the content of homologs containing more than n+3 mol ethylene oxide and/or propylene oxide is preferably reduced by 30 to 90% and more especially by 50 to 75% compared with the products produced by the process mentioned above.

The alkoxylation products according to the invention may be adducts of ethylene oxide, propylene oxide or of mixtures of ethylene oxide and propylene oxide with fatty alcohols. In general, the better thickening properties are exhibited by products in which only ethylene oxide or an ethylene oxide/propylene oxide mixture consisting predominantly of ethylene oxide is added onto the fatty alcohol. Accordingly, the use of these products is preferred, the use of pure ethoxylation products being particularly preferred.

Among the adducts of ethylene oxide with fatty alcohols, the best thickening properties are exhibited by those products which are insoluble or very poorly soluble in water at 20° C. Nevertheless, these products can be solubilized by the surfactant to be thickened.

The thickeners according to the invention may be prepared by various methods.

Thus, it is possible initially to prepare adducts of broad homolog distribution by known methods, for example by reaction of the fatty alcohols with ethylene oxide and/or propylene oxide under the catalytic effect of alkali metal alcoholates, such as sodium methylate, or alkali metal hydroxides. The higher homologs formed may then be separated off by physical and/or chemical separation techniques until products having the desired homolog distribution are present. Distillation is a simple and comparatively inexpensive separation process.

However, it is preferred to ensure, by appropriate choice of the catalyst system used in the preparation of the adducts, that the product mixture has a narrow homolog distribution. Thus, it is known, for example from European patent specifications 6 105, 26 544, 26 546, 82 569, 92 256 and 115 083, that products of narrow homolog distribution can be obtained by using alkaline earth metal oxides, hydroxides or alkoxides, optionally in combination with cocatalysts and promoters, as catalysts. German patent application P 37 06 047.3 describes alkaline earth metal salts of vicinally hydroxy,alkoxy-substituted fatty acids of which the use as catalysts in alkoxylation reactions leads to products of narrow homolog distribution. The use of alkaline earth metal salts of ether carboxylic acids as catalysts also leads to products having a narrow homolog distribution, as known from German patent applications P 37 19 968.4 and P 38 02 044.0. According to the teachings of other German patent applications, the use of the following alkoxylation catalysts also leads to very narrow homolog distributions: esters of titanic and/or zirconic acid with monoalkanols in combination with sulfuric acid and/or alkanesulfonic acids and/or hydroxyalkylsulfonic acids (P 38 14 849.8), alkaline earth metal salts of polycarboxylic acid monoesters (P 38 12 168.9) and also hydrotalcite (P 38 13 910.3).

Although the production of alkoxylation products having a narrow homolog distribution is described in a number of publications, there is no reference in any of those publications to the excellent thickening effect of these products.

In many cases, it has been found, the products obtained with the catalysts mentioned already possess such narrow homolog distributions that they may be directly used as thickeners in the surfactant solutions according to the invention. However, it may be necessary in individual cases, by applying the separation techniques mentioned above, to even further reduce the proportion of alkoxylation products containing more than n+3 mol ethylene oxide and/or propylene oxide until the products satisfy the requirements according to the invention.

Alkoxylation products having average degrees of alkoxylation of 2 to 5, and more especially 2 to 4, have proved to be particularly suitable thickeners. The use of these compounds in the surfactant solutions according to the invention is thus preferred.

The alkoxylation products are based on saturated and/or olefinically unsaturated $C_{8-22}$ fatty alcohols. These fatty alcohols may have both branched and also unbranched carbon chains. However, the unbranched fatty alcohols are preferably used by virtue of the better thickening properties of their alkoxylation products. It is possible to use pure fatty alcohols or mixtures of various fatty alcohols. Fatty alcohols obtained from natural raw materials, such as natural fats and oils, will generally be used. Accordingly, fatty alcohol mixtures having an origin-dependent distribution of the carbon chain lengths will be obtained in that case. If desired, it is possible by choosing suitable catalysts to ensure that ethylenic double bonds present in the carbon chains are only negligibly hydrogenated, if at all, during the reducing conversion of the carboxylic acid group into the alcohol group. It is preferred to use fatty alcohol mixtures which predominantly contain $C_{12-18}$ and more especially $C_{16-18}$ fatty alcohols. Mixtures such as these may be obtained, for example, from coconut oil, rapeseed oil or beef tallow and are marketed by Assignee under such trade names as "Ocenol" and "Lorol".

The thickened aqueous surfactant solutions according to the invention normally contain 3 to 30% by weight ionic surfactants, 0.5 to 5% by weight water-soluble organic thickeners and 0 to 10% by weight water-soluble inorganic and/or organic electrolyte salts.

The water-soluble ionic surfactants present may be anionic, zwitter-ionic and cationic surfactants. Suitable ionic surfactants are distinguished by a lipophilic, preferably linear $C_{8-18}$ alkyl or alkenyl group and, preferably attached terminally thereto, an ionic group dissociating in water. The anionic group may be, for example, a sulfate ($-OSO_3^-$), sulfonate ($-SO_3^-$), phosphate ($-O-PO_3^{--}$) or carboxylate ($-COO^-$) group; the cationic group may be, for example, a quaternary ammonium group (for example $-N^+(CH_3)_3$) and the zwitter-ionic groups may be, for example, $-N^+(CH_3)_2-CH_2-COO^-$ or

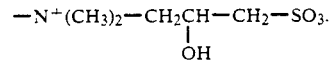

Suitable and preferred anionic surfactants include, for example, alkyl sulfates, alkyl polyglycol ether sulfates, alkanesulfonates, sulfosuccinic acid monoalkyl ester and monopolyethoxy alkyl ester, monoalkyl phosphates, protein fatty acid condensates, acyl isethionates, acyl taurides, soaps, alkyl ether carboxylic acids and acyl sarcosides. Suitable cationic surfactants are, for example, alkyl trimethyl ammonium halides, dialkyl dimethyl ammonium halides, alkyl dimethyl benzyl ammonium halides, alkyl pyridinium halides and alkyl imidazolinium halides. Suitable zwitter-ionic surfactants include, for example, N-alkyl-N,N-dimethyl glycine or N-acylaminopropyl-N,N-dimethylglycine, also alkylaminocarboxylic acids of the type obtained in the reaction of condensates of fatty acids with aminoethyl ethanolamines ("imidazolines") with sodium chloroacetate, etc. Mixtures of the anionic surfactants mentioned or mixtures of anionic or cationic and zwitterionic surfactants may also be used as the ionic surfactants.

The increase in viscosity of aqueous solutions of the type mentioned with their comparatively low content of ionic surfactants is of particularly high interest in terms of application. In such cases, the addition of the thickeners selected in accordance with the invention synergistically improves the thickenability of the solutions with inorganic electrolyte salts.

Suitable inorganic electrolyte salts include any water-soluble alkali metal, ammonium and alkaline earth salts, for example the fluorides, chlorides, bromides, sulfates, phosphates, nitrates, providing they are soluble in water in a quantity of at least 1% by weight at a temperature of 20° C. The chlorides or sulfates of an alkali metal, ammonium or magnesium are preferably used. Sodium chloride and magnesium chloride are particularly preferred.

Particularly suitable organic electrolyte salts include any water-soluble alkali, ammonium and alkaline metal earth salts of mono-, di- and tricarboxylic acids. Preference is attributed to carboxylic acids having a molecular weight less than 200 g/mol, for example succinic acid, tartaric acid and glutaric acid. Mixtures of these salts may also be used in accordance with the invention.

In addition, the aqueous preparations according to the invention may contain other components which make them suitable for the particular application under consideration. For example, they may contain nonionic surfactants, preferably in relatively small quantities to at most about 50% by weight of the ionic surfactants present. Finally, they may contain perfumes, dyes, opacifiers and pearlescers, antimicrobial agents, preservatives, skin-emollient agents, plant extracts, protein hydrolyzates, buffers, complexing agents and other known auxiliaries and additives of the type normally present in shampoos, bath additives, shower bath preparations, liquid soaps, liquid skin cleansers, liquid hair rinses, and also in liquid laundry and dishwashing detergents and liquid domestic cleaning preparations based on ionic surfactants.

The following Examples are intended to illustrate the invention without limiting it in any way.

EXAMPLES

I. FATTY ALCOHOLS USED

The alkoxylation products used in the Examples are based on the following fatty alcohols:

1. Lorol Special

"LOROL SPEZIAL" is the brand name of a mixture of fatty alcohols marketed by Assignee with the following C (carbon) chain distribution:

| C chain | Specification (% by weight) | Typical content |
|---|---|---|
| C-10 | 0–2 | approx. 1 |
| C-12 | 70–75 | approx. 72 |
| C-14 | 25–30 | approx. 26 |
| C-16 | 0–2 | approx. 1 |

2. "Rübocenol"

The C chain length distribution of this unsaturated fatty alcohol obtained from low-erucic rapeseed oil corresponds substantially to the following composition:

| C chain | % by weight |
|---|---|
| C-16 | approx. 7.0 |
| C-16' | approx. 2.0 (palmitoleyl alcohol) |
| C-18 | approx. 3.0 |
| C-18' | approx. 70.0 (oleyl alcohol) |
| C-18'' | approx. 8.0 (linoleyl alcohol) |
| C-18''' | approx. 7.0 (linolenyl alcohol) |
| C-20 | approx. 3.0 |

3. HD-Ocenol 50/55

The C chain distribution of the product marketed by Assignee under this name, a mixture of substantially unsaturated fatty alcohols, is as follows:

| C chain | Specification (% by weight) | Typical content |
|---|---|---|
| C-12 | 0–2 | approx. 1 |
| C-14 | 2–7 | approx. 5 |
| C-16 | 25–35 | approx. 30 |
| C-18 |  | approx. 20 |
| C-18' |  | approx. 41 |
| C-18'' | 55–75 | approx. 1 |
| C-18''' |  | approx. 1 |
| C-20 | 0–2 | approx. 1 |

In these Tables, the particular number of ethylenic double bonds present is represented by the number of apostrophes.

II. ALKOXYLATION PRODUCTS

Ethoxylated products were produced as follows from the afore-mentioned fatty alcohols The catalyst system (approx. 0.1 to 1% by weight, based on the end product) was added to the alcohol to be ethoxylated and the mass transferred to a suitable autoclave. After purging with nitrogen, the autoclave was evacuated for about 30 minutes at a temperature of 100° C. The temperature was then increased to 180° C. and the necessary quantity of ethylene oxide (EO) introduced up to a maximum pressure of 5 bar. On completion of the reaction, the reaction mixture was left to after-react for 30 minutes and the rest of the ethylene oxide was removed at 100° C. under a pressure of 14 mbar.

The thickeners prepared for the Examples and Comparison Examples are shown in Table 1.

TABLE 1

| Thickener | Fatty alcohol | n | Catalyst |
|---|---|---|---|
| B 1 | Lorol Spezial | 3 | Calcium salt of an alkoxy hydroxy fatty acid[1] |
| V 1 | Lorol Spezial | 3 | Sodium methylate |
| B 2a | Eübocenol | 3.5 | Calcium salicylate |
| B 2b | Eübocenol | 3.5 | Hydrotalcite[2] |
| V 2 | Rübocenol | 3.5 | Sodium methylate |
| B 3 | HD-Ocenol 50/55 | 3 | Alkaline earth salt of an ether carboxylic acid[3] |
| V 3 | HD-Ocenol 50/55 | 3 | Sodium methylate |
| B 4 | Lorol Spezial | 2.5 | Hydrotalcite[2] |
| V 4 | Lorol Special | 2.5 | Sodium methylate |

[1] according to German patent application P 37 06 047.3
[2] according to German patent application P 38 13 910.3
[3] according to German patent application P 37 19 968.4

The homolog distribution of the products obtained is shown in Table 2. The data were obtained as follows:

The terminal hydroxyl groups of the alkoxylation products were reacted with acetyl chloride to the acetates by known methods to increase the volatility of the compounds. For the gas-chromatographic separation of the homologs, 1 μl of a 11% solution of the acetates in isooctane was separated in a 2 meter long glass column of which the stationary phase consisted of 3% SE 30

(methyl silicone gum, a Supelco product) on Chromosorb GAWDMCS (Kieselgur G, a diatomaceous earth, treated with hydrochloric acid and then with dimethyl chlorosilane to change the polar OH groups on the surface to nonpolar dimethyl silane groups, a Waters product). Nitrogen was used as the carrier gas (throughflow rate 25 ml/min.). During separation, the temperature of the column was increased from 120° C. to 300° C. at a rate of 4° C. per minute. A flame ionization detector (Packard 438) was used to detect the products separated.

TABLE 2

| Substance | Percentage area | | | | | | | | |
|---|---|---|---|---|---|---|---|---|---|
| | B 1 | V 1 | B 2a | B 2b | V 2 | B 3 | V 3 | B 4 | V 4 |
| Free fatty alcohol | 14.0 | 21.5 | 10.8 | 5.6 | 18.1 | 17.0 | 18.6 | 12.1 | 26.2 |
| Fatty alcohol + 1 EO | 10.5 | 13.7 | 7.9 | 7.0 | 10.7 | 11.3 | 11.3 | 15.8 | 16.9 |
| Fatty alcohol + 2 EO | 14.2 | 12.4 | 11.1 | 10.0 | 10.4 | 14.1 | 10.6 | 22.9 | 14.9 |
| Fatty alcohol + 3 EO | 16.5 | 10.8 | 14.6 | 20.3 | 10.2 | 15.7 | 9.6 | 24.1 | 12.0 |
| Fatty alcohol + 4 EO | 15.7 | 9.1 | 13.3 | 19.7 | 9.0 | 14.2 | 7.9 | 15.2 | 9.3 |
| Fatty alcohol + 5 EO | 12.0 | 7.0 | 10.0 | 13.6 | 7.2 | 5.7 | 6.4 | 6.2 | 6.6 |
| Fatty alcohol + 6 EO | 7.4 | 5.8 | 6.0 | 7.4 | 6.2 | 3.5 | 5.6 | 1.9 | 4.9 |
| Fatty alcohol + 7 EO | 3.8 | 4.7 | 3.1 | 3.1 | 5.1 | 1.7 | 4.4 | 0.6 | 3.4 |
| Fatty alcohol + 8 EO | 1.7 | 3.6 | 1.2 | 1.0 | 4.1 | 1.4 | 3.4 | 0.2 | 2.3 |
| Fatty alcohol + 9 EO | 0.8 | 2.7 | 0.4 | 0.5 | 3.0 | 0.5 | 2.5 | 0.1 | 1.3 |
| Fatty alcohol + 10 EO | 0.2 | 1.9 | 0.2 | 0.3 | 1.8 | 0.4 | 1.7 | 0.2 | |
| Fatty alcohol + 11 EO | — | 1.2 | 0.1 | 0.2 | 1.0 | 0.3 | 1.3 | 0.1 | |
| Fatty alcohol + 12 EO | — | 0.8 | — | 0.1 | 0.5 | 0.2 | 0.9 | 0.1 | |
| Fatty alcohol + 13 EO | — | 0.4 | — | — | 0.1 | 0.4 | 0.7 | | |
| Fatty alcohol + 14 EO | — | 0.2 | — | — | — | 0.2 | 0.2 | | |

III. PERFORMANCE TESTING OF THE SURFACTANT SOLUTIONS

The particular viscosities spontaneously adjusted in aqueous solutions having the following basic composition were determined.

10% by weight ether sulfate (surfactant)
3% by weight thickener
x% by weight NaCl The ether sulfate surfactant used for the performance testing was "Texapon NSO", a product marketed by Applicant (fatty alcohol $C_{12-14}$ (70:30) polyglycol ether-(2EO)-sulfate sodium salt, 28%/wt in water).

The viscosity values of the surfactant solutions containing the narrow-range thickener (B1-B3), as determined with a Höppler falling ball viscosimeter at 20° C., are shown in Table 3. Comparison with the values obtained where the wide-range thickener (V1-V3) is sued shows the advantages of the thickeners according to the invention.

TABLE 3

| Thickener | NaCl content × (% by weight) | Viscosity (mPa · s) | Cloud point (°C.) | Clear point (°C.) |
|---|---|---|---|---|
| B 1 | 2.0 | 25.000 | 0 | 14 |
| V 1 | 2.0 | 16.000 | 7 | 19 |
| B 2 a | 2.5 | 43.000 | 10 | 25 |
| B 2b | 2.75 | 62.000 | 11 | 23 |
| V 2 | 3.0 | 37.000 | 7 | 26.5 |
| B 3 | 2.5 | 60.000 | 20 | 25 |
| V 3 | 2.5 | 36.000 | 20 | 26.5 |
| B 4 | 1.5 | 41.200 | 6 | 23 |
| V 4 | 1.5 | 4.900 | | |

We claim:

1. An aqueous solution consisting of from about 3 to 30% by weight of a water-soluble ionic surfactant selected from an anionic, switterionic and cationic surfactant, said solution having been thickened with a thickener consisting of from about 0.5 to about 5% by weight, based on the weight of said solution, of an adduct of ethylene oxide or propylene oxide with a saturated or unsaturated $C_{8-22}$ fatty alcohol having an average degree of alkoxylation n of about 1 to about 10 wherein the homolog or oligomer content of n+3 moles of ethylene oxide or propylene oxide of said adduct has been reduced by more than about 10% by weight, based on the weight of said adduct, and from 0 to about 10% by weight, based on the weight of said solution, of a water-soluble electrolyte salt.

2. An aqueous solution as in claim 1 wherein the homolog or oligomer content of n+3 moles of ethylene oxide or propylene oxide of said adduct has been reduced by more than about 30% by weight, based on the weight of said adduct.

3. An aqueous solution as in claim 1 wherein the homolog or oligomer content of n+3 moles of ethylene oxide or propylene oxide of said adduct has been reduced by more than about 50% by weight, based on the weight of said adduct.

4. An aqueous solution as in claim 1 wherein the homolog or oligomer content of n+3 moles of ethylene oxide or propylene oxide of said adduct has been reduced by about 30 to about 90% by weight, based on the weight of said adduct.

5. An aqueous solution as in claim 1 wherein said fatty alcohol has an average degree of alkoxylation n of about 1 to about 6.

6. An aqueous solution as in claim 1 wherein said adduct is insoluble or substantially insoluble in water at about 20° C.

7. The process of increasing the viscosity of an aqueous solution consisting of from about 3 to about 30% by weight of a water-soluble ionic surfactant selected from an anionic, zwitterionic and cationic surfactant, comprising adding to said solution from about 0.5 to about 5% by weight, based on the weight of said solution, of a thickener consisting of an adduct of ethylene oxide or propylene oxide with a saturated or unsaturated $C_{8-22}$ fatty alcohol having an average degree of alkoxylation n of about 1 to about 10 wherein the homolog or oligomer content of n+3 moles of ethylene oxide or propylene oxide of said adduct has been reduced by more than about 10% by weight, based on the weight of said adduct, and from 0 to about 10% by weight, based on the weight of said solution, of a water-soluble electrolyte salt.

8. A process as in claim 7 wherein the homolog or oligomer content of n+3 moles of ethylene oxide or propylene oxide of said adduct has been reduced by more than about 30% by weight, based on the weight of said adduct.

9. The process as in claim 7 wherein the homolog or oligomer content of n+3 moles of ethylene oxide or propylene oxide of said adduct has been reduced by more than about 50% by weight, based on the weight of said adduct.

10. The process as in claim 7 wherein the homolog or oligomer content of n+3 moles of ethylene oxide or propylene oxide of said adduct has been reduced by about 30 to about 90% by weight, based on the weight of said adduct.

11. The process as in claim 7 wherein said fatty alcohol has an average degree of alkoxylation n of about 1 to about 6.

12. An aqueous solution as in claim 1 wherein said surfactant comprises an ether sulfate.

13. The process as in claim 7 wherein said surfactant comprises an ether sulfate.

* * * * *